United States Patent [19]

Igarashi et al.

[11] 4,200,628
[45] Apr. 29, 1980

[54] NOVEL AMINOGLYCOSIDE DERIVATIVES

[75] Inventors: Kikuo Igarashi, Itami; Junji Irisawa, Nishinomiya; Tsunetoshi Honma, Ikoma, all of Japan

[73] Assignee: Shionogi & Co., Ltd., Dosho, Japan

[21] Appl. No.: 944,065

[22] Filed: Sep. 19, 1978

[30] Foreign Application Priority Data

Oct. 25, 1977 [JP] Japan ................... 52-128447

[51] Int. Cl.$^2$ .................. A61K 31/71; C07H 15/22
[52] U.S. Cl. .................. 424/180; 536/17 R
[58] Field of Search .................. 536/17; 424/180

[56] References Cited

U.S. PATENT DOCUMENTS

| | | | |
|---|---|---|---|
| 3,808,198 | 4/1974 | Naito et al. | 536/17 |
| 4,001,208 | 1/1977 | Umezawa et al. | 536/17 |
| 4,117,221 | 9/1978 | Daniels | 536/17 |

*Primary Examiner*—Johnnie R. Brown
*Attorney, Agent, or Firm*—Wenderoth, Lind & Ponack

[57] ABSTRACT

Novel aminoglycoside derivatives and their salts containing 2-deoxystreptamine moiety, of which the 1-amino group is acylated by a group represented by the formula:

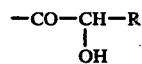

(wherein R is 4 to 6 membered heterocyclic group containing 1 to 2 nitrogen atoms which may optionally be substituted.) effective in treatment of infectious diseases caused by gram positive and gram negative bacteria.

19 Claims, No Drawings

NOVEL AMINOGLYCOSIDE DERIVATIVES

BACKGROUND OF THE INVENTION

Aminoglycoside antibiotics, for example, streptomycins, kanamycins, gentamicins, tobramycin etc. have practically been used as broad spectrum antimicrobials effective against gram-positive, gram-negative and acid-fast bacteria. The aminoglycoside antibiotics, however, are sometimes accompanied by undesired side effect such as nephropathy and deafness. Occurrence of resistant strains against the aminoglycosides is another problem to be solved. It has been attempted to modify such aminoglycosides with a specified acyl group at the 1-amino group in order to improve the antimicrobial activity and relatively decrease the side effect. For instance, amikacin, an excellent antimicrobial agent, which is prepared by acylation of the 1-amino group of kanamycin A with L-(—)-4-amino-2-hydroxybutyric acid, is effective against kanamycin A resistant strains and its toxicity is approximately the same as kanamycin A [described in J. Antibiotic, 25, 695 (1972) by Kawaguchi et al; U.S. Pat. No. 3,781,268 and J. Antibiotic, 27, 677 (1974) by Fujisawa et al].

The present inventors have found that the antimicrobial spectrum and the potency of activity are improved by acylation of the 1-amino group of aminoglycosides with α-hydroxy-α-heterocycleacetic acids. The present invention is based upon this finding.

SUMMARY OF THE INVENTION

This invention relates to novel aminoglycoside derivatives having an excellent antimicrobial action. More particularly, this invention relates to novel aminoglycoside antibiotic derivatives and their salts containing a 2-deoxystreptamine moiety of which the 1-amino group is acylated by α-hydroxy-α-heterocycleacetic acid.

The novel aminoglycoside antibiotic derivatives in this invention can be represented by the formula:

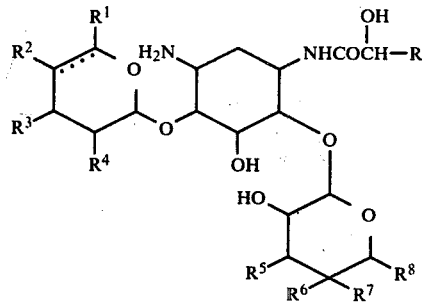

(wherein
R is 4 to 6 membered heterocyclic group containing 1 to 2 nitrogen atoms which may optionally be substituted;
$R^1$ is aminomethyl, hydroxymethyl, 1-aminoethyl, or 1-methylaminoethyl;
$R^2$, $R^3$ and $R^6$ each is hydrogen or hydroxy;
$R^4$ is hydroxy or amino;
$R^5$ is amino or methylamino;
$R^7$ is hydroxy or methyl;
$R^8$ is hydrogen, hydroxymethyl, or carbamoyloxymethyl; and
the dotted line represents the presence or absence of a double bond.)

The aminoglycosides used as starting material in this invention containing 2-deoxystreptamine moiety are represented by the general formula (II):

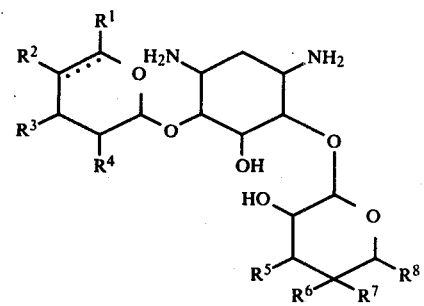

(wherein $R^1$, $R^2$, $R^3$, $R^4$, $R^5$, $R^6$, $R^7$, $R^8$ and the dotted line have the same meaning as mentioned above.) Representative of the compounds (II) and their substituents are shown in Table 1.

Table 1

| Generic Name | $R^1$ | $R^2$ | $R^3$ | $R^4$ | $R^5$ | $R^6$ | $R^7$ | $R^8$ | dotted line |
|---|---|---|---|---|---|---|---|---|---|
| tobramycin | $CH_2NH_2$ | OH | H | $NH_2$ | $NH_2$ | H | OH | $CH_2OH$ | none |
| kanamycin A | " | " | OH | OH | " | " | " | " | " |
| kanamycin B | " | " | " | $NH_2$ | " | " | " | " | " |
| kanamycin C | $CH_2OH$ | " | " | " | " | " | " | " | " |
| deoxykanamycin A | $CH_2NH_2$ | " | H | OH | " | " | " | " | " |
| dideoxykanamycin B (dibekacin) | " | H | " | $NH_2$ | " | " | " | " | " |
| gentamicin $C_1$ | $CH(CH_3)NHCH_3$ | " | " | " | $NHCH_3$ | OH | $CH_3$ | H | " |
| gentamicin $C_2$ | $CH(CH_3)NH_2$ | " | " | " | " | " | " | " | " |
| gentamicin $C_{1a}$ | $CH_2NH_2$ | " | " | " | " | " | " | " | " |
| gentamicin B | " | " | OH | OH | " | " | " | " | " |
| nebramycin factor 4 | " | OH | " | $NH_2$ | $NH_2$ | H | OH | $CH_2OCONH_2$ | " |
| nebramycin factor 5' | " | " | H | " | " | " | " | " | " |
| sisomicin | " | H | " | " | $NHCH_3$ | OH | $CH_3$ | H | double bond |

DETAILED EXPLANATION

In the aforementioned general formula (I), the 4- to 6-membered heterocyclic groups as R include 2-azetidinyl, 3-azetidinyl, 2-pyrrolyl, 3-pyrrolyl, 2-pyrrolinyl, 3-pyrrolinyl, 2-pyrrolidinyl, 3-pyrrolidinyl, 2-imidazolyl, 4-imidazolyl, 2-imidazolinyl, 4-imidazolinyl, 2-imidazolidinyl, 4-imidazolidinyl, 3-pyrazolyl, 4-pyrazolyl, 3-pyrazolinyl, 4-pyrazolinyl, 3-pyrazolidinyl, 4-pyrazolidinyl, 2-pyridyl, 3-pyridyl, 4-pyridyl, 2-piperidyl, 3-piperidyl, 4-piperidyl, 3-pyridazinyl, 4-pyridazinyl, 2-pyrimidinyl, 4-pyrimidinyl, 5-pyrimidinyl, 2-pyrazinyl, 3-pyrazinyl, 2-piperazinyl, 3-piperazinyl and the like. These heterocyclic groups may optionally be substituted.

The novel aminoglycoside antibiotic derivatives (I) in this invention include the free bases and salts thereof, particularly non-toxic acid addition salts, for example, salts with inorganic acids such as hydrochloric acid, hydrobromic acid, hydroiodic acid, sulfuric acid, phosphoric acid, carbonic acid, and the like, and salts with organic acids such as acetic acid, fumaric acid, malic acid, tartaric acid, maleic acid, citric acid, mandelic acid, ascorbic acid, gallic acid, and the like.

Representative of the compounds (I) are:

(1) 1-N-[2-hydroxy-2-(azetidin-3-yl)acetyl]tobramycin
(2) 1-N-[2-hydroxy-2-(pyrrolidin-2-yl)acetyl]tobramycin
(3) 1-N-[2-hydroxy-2-(pyrrolidin-3-yl)acetyl]tobramycin
(4) 1-N-[2-hydroxy-2-(piperidin-3-yl)acetyl]tobramycin
(5) 1-N-[2-hydroxy-2-(piperazin-2-yl)acetyl]tobramycin
(6) 1-N-[2-hydroxy-2-(azetidin-2-yl)acetyl]tobramycin

PREPARATION

Compounds (I) may readily be prepared by acylating the aforementioned aminoglycosides (II) with carboxylic acids represented by the formula:

$$\underset{R-CHCOOH}{\overset{OH}{|}} \quad (III)$$

(wherein R has the same meaning as mentioned above.) or the reactive derivatives thereof.

Since the starting aminoglycosides (II) have many functional groups (e.g. amino groups) other than the 1-amino group to be acylated, it is appropriate to optionally protect them by protecting groups by acylation. All of the protecting groups ordinarily used in peptide synthesis, which may readily be removed after acylation of the 1-amino group, may be employed. Such protecting groups include benzyloxycarbonyl which may optionally be substituted on the benzene nucleus, formyl, t-butoxycarbonyl, t-amyloxycarbonyl, methoxycarbonyl, ethoxycarbonyl, p-toluenesulfonyl, phthaloyl, m-nitrophenylthio, triphenylmethylthio, and the like.

The reactive derivatives of the above mentioned carboxylic acids used as acylating agents include those ordinarily used in peptide synthesis, for example, acid halides, acid azides, acid anhydrides, mixed acid anhydrides, reactive esters and the like. Examples of these derivatives have been described in Synthesis Volume 453 (1972) and Peptide Synthesis Volume 75 to 135 (1966) by M. Bodanszky et al. In the acylating agents, when R has a susceptible imino group, it is desirable to protect it by a suitable protecting group, for example, the same ones as mentioned in the aminoglycoside protection. The acylating agents (III) may be prepared according to the following reaction scheme.

Reaction Scheme

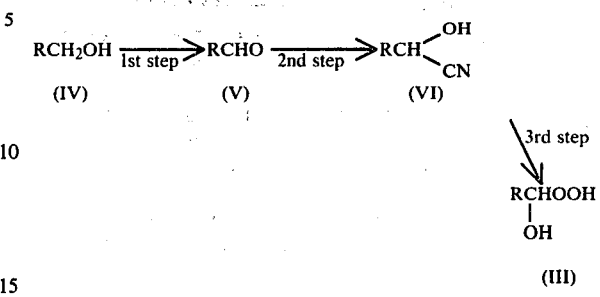

(wherein R has the same meaning as mentioned above.) This process consists of 3 steps, that is, 1st step of oxidation of the starting materials (IV), 2nd step of cyanohydrin formation, and 3rd step of hydrolysis of the cyano group. The starting materials (IV) are well-known compounds, for instance, the compound wherein R is 2-pyrrolidinyl has been described in J. Org. Chem., 32, 2388 (1967) by P. G. Gassman and A. Fentiman.

(First Step) Oxidation

The oxidation is carried out in the conventional manners usually employed in oxidation of primary alcohols to aldehydes, such as Oppenauer oxidation or oxidation with oxidizing agents, e.g. chromic acid-pyridine complex, Jones reagent, dimethylsulfoxide-dicyclohexylcarbodiimide, and the like. In this invention, the oxidation with dimethylsulfoxide-dicyclohexylcarbodiimide is most preferably employed. When dimethylsulfoxide-dicyclohexylcarbodiimide is employed as an oxidizing agent, the reaction is conducted at a temperature of −10° C. to 40° C., preferably 0° C. to 20° C. If required, the reaction may be accelerated on addition of phosphoric acid or phosphorus pentachloride to the reaction medium.

(Second Step) Cyanohydrin Formation

This step is effected by cyanation of the compounds (V) with a cyanating agent. The cyanating agents include hydrogen cyanide, sodium cyanide, potassium cyanide, and the like cyanating agents ordinarily employed in cyanohydrin formation. The reaction proceeds well even at room temperature, but if required, it may be accelerated by heating.

(Third Step)

The hydrolysis of the compounds (VI) is effected with an acid or alkali. The acids include those used in ordinal hydrolysis of nitriles, for example, hydrochloric acid and sulfuric acid. The alkalis include sodium hydroxide, potassium hydroxide and the like. The reaction may be conducted at a temperature of 0° C. to 100° C., preferably at 80° C. to 100° C.

The acylation of aminoglycosides in this invention is achieved by reacting the starting aminoglycosides (II), of which the functional groups other than the 1-amino group have been protected, with the above acylating agent in a suitable solvent. Examples of the solvent employed are alcohols (e.g. methanol, ethanol), ethers (e.g. diethyl ether, 1,2-dimethoxyethane, tetrahydrofuran, dioxane), ketones (e.g. acetone, methyl ethyl ketone), dimethylformamide, dimethylacetamide, pyridine, water and the like, and they may be used alone or as a mixture of two more kinds of them. In carrying out the acylation, an equimolar amount or an excess amount of acylating agent, preferably about 1.0 to 2.0 moles, is used to one mole of aminoglycosides (II). The reaction is conducted at a temperature of −20° C. to 50° C., preferably 0° C. to 35° C., more preferably 20° C. to 25° C.

EFFECT

The aminoglycosides antibiotic derivatives and the non-toxic salts thereof prepared in this invention exhibit excellent antimicrobial activities. They are several to several ten times more active than the corresponding unacylated aminoglycosides against some species of gram positive and gram negative bacteria. Minimum Inhibitory Concentration (MIC, μg/ml) of the acylated compounds of this invention and the corresponding well-known unacylated aminoglycosides is indicated in Table 2.

Table 2

| Bacteria | MIC (μg/ml) Test Compounds No. | | | | | | | | | |
|---|---|---|---|---|---|---|---|---|---|---|
| | (1) | (2) | (3) | (4) | (5) | (6) | (7) | (8) | (9) | TOB |
| *Staphylococcus aureus* FDAJC | 0.1 | 0.1 | 0.1 | 0.1 | 0.1 | 0.1 | 0.4 | 0.1 | 0.1 | 0.05 |
| *Staphylococcus epidermidis* TB-775* | 6.2 | 100.0 | 6.2 | 25.0 | 100.0 | 50.0 | >100.0 | 25.0 | 50.0 | 100.0 |
| *Escherichia coli* NIHJ JC-2 | 1.6 | 6.2 | 0.4 | 1.6 | 12.5 | 0.8 | 50.0 | 1.6 | 25.0 | 0.78 |
| *Escherichia coli* W-677/JR-762* | 6.2 | 6.2 | 1.6 | >100.0 | 25.0 | 3.1 | 100.0 | 3.1 | 25.0 | 100.0 |
| *Klebsiella pneumoniae* K1-38 | 0.8 | 1.6 | 0.4 | 1.6 | 6.2 | 0.8 | 12.5 | 0.8 | 6.2 | 3.13 |
| *Enterobacter cloacae* TB-718 | 1.6 | 3.1 | 0.4 | 1.6 | 6.2 | 0.8 | 25.0 | 0.8 | 12.5 | 0.78 |
| *Serratia marcescens* ATCC 13880 | 12.5 | 50.0 | 6.2 | 25.0 | 100.0 | 25.0 | >100.0 | 25.0 | 100.0 | 3.13 |
| *Proteus vulgaris* TB-615* | 12.5 | >100.0 | 12.5 | 25.0 | 100.0 | 25.0 | >100.0 | 12.5 | 50.0 | 25.0 |
| *Proteus mirabilis* TB-617 | 3.1 | 3.1 | 0.8 | 3.1 | 6.2 | 0.8 | 12.5 | 1.6 | 6.2 | 12.5 |
| *Proteus rettgeri* Ret 40 | 0.8 | 0.8 | 0.4 | 1.6 | 3.1 | 0.2 | 6.2 | 0.8 | 3.1 | 0.39 |
| *Proteus inconstans* In-27* | 100.0 | >100 | 50.0 | >100.0 | >100.0 | >100.0 | >100.0 | 100.0 | >100.0 | 12.5 |
| *Pseudomonas aeruginosa* Ps-24 | 1.6 | 1.6 | 0.4 | 12.5 | 6.2 | 1.6 | 12.5 | 0.8 | 3.1 | 0.39 |
| *Pseudomonas aeruginosa* PP-6* | 3.1 | 12.5 | 1.6 | 25.0 | 25.0 | 6.2 | 50.0 | 12.5 | 25.0 | 50 |
| *Pseudomonas aeruginosa* TB-121* | 6.2 | 12.5 | 3.1 | 25.0 | 25.0 | 6.2 | 100.0 | 6.2 | 12.5 | 100.0 |
| *Pseudomonas aeriginosa* TB-151* | 6.2 | 12.5 | 3.1 | 25.0 | 100.0 | 12.5 | 50.0 | 6.2 | 25.0 | 100.0 |

(Note)
(1) = 1-N-[2-hydroxy-2-(pyrrolidin-3-yl)acetyl]tobramycin
(2) = 1-N-[2-hydroxy-2-(azetidin-2-yl)acetyl]tobramycin
(3) = 1-N-[2-hydroxy-2-(azetidin-3-yl)acetyl]tobramycin
(4) = 1-N-[2-hydroxy-2-(piperidin-3-yl)acetyl]tobramycin
(5), (6) and (7) = 1-N-[2-hydroxy-2-(pyrrolidin-2-yl)acetyl]tobramycin
(8) and (9) = 1-N-[2-hydroxy-2-piperazin-2-yl)acetyl]tobramycin
TOB = tobramycin
*represents tobramycin resistant strains.

As seen from Table 2, the compounds (I) of this invention are valuable antimicrobial agents effective against various species of gram positive and negative bacteria, and useful as drugs used for humans and other various kinds of animals. They can be used in the treatment of infectious diseases caused by aminoglycoside sensitive strains and resistant strains (e.g. *staphylococcus epidermidis, Escherichia coli, Klebsiella pneumoniae, Pseudomonas aeruginosa, Proteus mirabilis*).

The compounds (I) of this invention can also be used as disinfectants for preventing the growth of bacteria alive in perishable, feedstuffs, or hygenical materials.

HOW TO USE

The compounds (I) of this invention can be in a wide variety of oral or parenteral dosage forms solely or in admixture with other co-acting substances. The pharmaceutical compositions may be a mixture of 0.01 to 99% of the compounds (I) with a pharmaceutical carrier or carriers which can be a solid material or liquid material in which the compounds (I) are soluble, dispersible, or suspensible. They can be in a unit dosage form. The solid compositions can be in forms of tablets, powder, dry syrups, troches, granules, capsules, pills, suppositories, or like solid preparations. The liquid compositions can be in forms of injections, ointments, dispersions, inhalant, suspensions, solutions, emulsions, syrups, or elixirs. All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium arginate, tragacanth, carboxymethylcellulose, sorbitol, polyvinylpyrrolidone); disintegrators (e.g. starch, agar, carbonates, sodium laurylsulfate), lubricants (e.g. stearic acid, talc, paraffin, boric acid, silica, sodium benzoate, polyethyleneglycol, cacao oil, magnesium sulfate); emulsifying agents (e.g. lecithin, sorbitan monooleate, acacia); suspending agents (e.g. sorbitol, methylcellulose, glucose, sugar syrup, gelatin, hydroxymethylcellulose, carboxymethylcellulose, aluminium stearate gel, hydrogenated fats); solvents (e.g. water, peanut oil, sesame oil, methyl oleate); preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on the compounds (I).

The compound (I) of this invention, particularly, its sulfate, is readily soluble in water and conveniently used as a solution for intravenous, intramuscular, or subcutaneous injection according to a conventional method. The compound (I) can be dissolved in an aqueous or oily solvent for injection to give an injectable solution in an ampoule; in order to preserve the injectable preparation for a long period of time, it is appropriate to make a vial preparation containing crystalline, powder, microcrystalline, or lyophilizate of the compound (I). The vial preparation may be dissolved or suspended in the said solvent for injection immediately before use. The preparation may contain said preservatives.

Further, the compounds (I) of this invention can be used as suppositories, ointments for topical or opthalmic use, powders for topical use, and like preparations preparable according to the method well-known to those skilled in the art. The external preparation can contain 0.01 to 99% of the compound (I) of this invention together with a necessary amount of pharmaceutical carrier given above.

This invention also provides a method for treating infections caused by bacteria in humans or domestic animals, which comprises administering to the humans or animals the compound (I) of this invention at a divided or single dose of 0.01 to 5 g/kg a day for injection, 0.01 to 10 g/kg a day for oral aministration, or 0.01 to 10 g a day for a local application at intervals of 3 to 12 hours.

The method is applicable for treating some infectious diseases caused by bacteria sensitive to the compounds of this invention, e.g. staphylodermia, anthropozoonosis, cystitis, pyelitis, pneumonia, pneumonitis, bronchitis, empyematic, naspharyngitis, tonsilitis, rhinitis, dermatitis, pustulosis, abscess, wound and soft tissue infections, ear infections, osteomyelitis, septicemia, enteritis, urinary tract infections, and pyelonephritis.

Preferably, the compounds (I) of this invention are given to a patient in forms of pharmaceutical preparation, e.g. powder, dry syrup, tablets, troches, granules, capsules, pills, suppositories, injections, ointments, dispersions, inhalant, suspensions, solutions, emulsions, syrups and elixirs. They may be in a unit dosage form, e.g. tablets, troches, capsules, injections, vials, granules, or powder in a separate container of package.

The following examples are provided to further illustrate this invention.

EXAMPLE 1

Preparation of 2-hydroxy-2-(1-diphenylmethylazetidin-3-yl)acetic acid (1) To a solution of 2.39 g (1 mmole) of 1-diphenylmethyl-3-hydroxyazetidine [prepared in the manner described in J. C. S. Chem. Commun. 93 (1968) by S. S. Chatterjee and D. J. Triggle] in 30 ml of pyridine is added 3.8 g (2 equivalents) of p-toluenesulfonyl chloride, and the mixture is stirred at room temperature overnight and evaporated under reduced pressure. The residue is alkalified with an aqueous sodium carbonate solution and extracted with benzene. The extract is washed with water, dried over sodium sulfate, and evaporated under reduced pressure. The resulting brown oily residue (4.5 g) is adsorbed on a column of 20 g of silica gel and eluted with benzene. The eluate is crystallized from ether-hexane to yield 2.55 g of 1-diphenylmethyl-3-toluenesulfonylazetidine having mp. 108° to 110° C. as prisms in 64.8% yield, which is recrystallized from ether to yield the pure product having mp. 110° to 112° C.

IR: $\nu_{max}^{Nujol}$ 1370, 1355, 1185 cm$^{-1}$.

Elemental Analysis (for $C_{23}H_{23}NO_3S$): Calcd(%): C,70.20; H,5.89; N,3.56; S,8.15. Found(%): C,70.40; H,5.87; N,3.56; S,8.26.

(2) To a solution of 1.0 g. (2.54 mmoles) of 1-diphenylmethyl-3-toluenesulfonylazetidine in 10 ml of dimethylsulfoxide is added 547 mg (8.4 mmoles; 3.3 equivalents) of potassium cyanide, and the mixture is heated to 100° C. for 15 minutes. After cooling, the mixture is mixed with water and extracted with ether. The extract is washed with water, dried over sodium sulfate and evaporated under reduced pressure. The residue is dissolved in ether, treated with active carbon, and filtered. The filtrate is evaporated to yield 435 mg of 1-diphenylmethyl-3-cyanoazetidine having mp. 153° to 154° C. as needles in 69% yield. From the mother liquor, the same product having mp. 149° to 152° C. is obtained in 6.3% yield. Total yield is 75.3%. The product is recrystallized from ether to yield the pure product having mp. 158° to 159° C.

IR: $\nu_{max}^{Nujol}$ 2230 cm$^{-1}$.

Elemental Analysis (for $C_{17}H_{14}N_2$): Calcd(%): C, 82.22; H, 6.50; N, 11.28. Found(%): C, 82.36; H, 6.70; N, 11.05.

(3) A solution of 3.13 g (12.6 mmoles) of 1-diphenylmethyl-3-cyanoazetidine in 15 ml of a mixture of concentrated sulfuric acid and methanol (volume ratio=1:1) is heated to 100° C. for 30 minutes and after cooling, poured into a large amount of ice water and extracted with methylene chloride. The extract is washed with an aqueous sodium hydrogencarbonate solution and water, dried over sodium sulfate, and evaporated to yield 2.707 g of 1-diphenylmethyl-3-methoxycarbonylazetidine as crude product in 76.3% yield.

IR: $\nu_{max}^{Nujol}$ 1740 cm$^{-1}$.

NMR: $\delta_{ppm}^{CDCl_3}$ 3.5 (3H, s)

To a suspension of 0.36 g (3 equivalents) of lithium aluminium hydride in 20 ml of dry ether is dropwise added a solution of 3.6 g (12.7 mmoles) of crude 1-diphenylmethyl-3-methoxycarbonylazetidine in 20 ml of dry ether, and the mixture is stirred at room temperature for 15 minutes. The excess amount of lithium aluminium hydride is decomposed with ethyl acetate. The insoluble materials are filtered off and washed with dry ether. The combined filtrate and washings are evaporated under reduced pressure to yield the residue, which is dissolved in ether. The resulting solution is washed with an aqueous sodium hydrogencarbonate solution and then water, dried over sodium sulfate, and evaporated to yield 3.131 g of hemi-solid product, which is crystallized from ether to yield 1-diphenylmethyl-3-hydroxymethylazetidine as prisms.

First crystals: mp. 121° to 122° C.
Yield: 2.462 g (76.5%).
Second crystals: mp. 120° to 121° C.
Yield: 0.183 g (5.7%)
Total Yield: 82.2%

Elemental Analysis (for $C_{17}H_{19}NO$): Calcd(%): C, 80.57; H, 7.56; N, 5.53. Found(%): C, 80.80; H, 7.64; N, 5.43.

(4) To a solution of 2.27 g (8.96 mmoles) of 1-diphenylmethyl-3-hydroxymethylazetidine in 30 ml of dimethylsulfoxide are added 586 mg (0.67 equivalent) of phosphoric acid and 4.25 g (2.3 equivalents) of dicyclohexylcarbodiimide, and the mixture is stirred at room temperature overnight. The insoluble materials are filtered off, and the filtrate is alkalified with an aqueous sodium carbonate solution and extracted with ethyl acetate. The extract is reextracted three times with 14.9% aqueous sodium hydrogensulfite solution. The extract is alkalified with 10% aqueous sodium hydroxide solution and extracted with methylene chloride. The extract is dried and evaporated to yield 1.281 g of crude light yellow syrupy 1-diphenylmethyl-3-formylazetidine in 56.9% yield.

IR: $\nu_{max}^{film}$ 1720 cm$^{-1}$.

NMR: $\delta_{ppm}^{CDCl_3}$ 9.81 (1H, d, J=2 Hz).

(5) To a solution of 1.13 g (4.49 mmoles) of crude 1-diphenylmethyl-3-formylazetidine in a mixture of 2 ml of water and 2 ml of tetrahydrofuran is added 878 mg (3 equivalents) of potassium cyanide, and the mixture is stirred at room temperature for 2 hours, mixed with water and extracted with methylene chloride. The extract is washed with water, dried, and evaporated to yield 1.046 g of crude 2-hydroxy-2-(1-diphenylmethylazetidin-3-yl)acetonitrile as hemi-solid product in 83% yield.

NMR: $\delta_{ppm}^{CDCl_3}$ 4.60 (1H, d, J=6 Hz).

(6) A solution of 205 mg (0.74 mmole) of crude 2-hydroxy-2-(1-diphenylmethylazetidin-3-yl)acetonitrile in 1 ml of concentrated hydrochloric acid is heated to 85° C. for 2 hours. The excess amount of concentrated hydrochloric acid is removed off by evaporation under reduced pressure. The residue is dissolved in a small amount of a mixture of ammonium hydroxide and chloroform, and the resulting solution is evaporated under reduced pressure. The residue is mixed with a small amount of chloroform. The precipitate, which appears, is filtered off and the filtrate is evaporated under reduced pressure. The residue is dissolved in an aqueous dilute ammonium hydroxide, washed with ether, and evaporated under reduced pressure to yield 120 mg of 2-hydroxy-2-(1-diphenylmethylazetidin-3-yl)acetic acid as powder in 54% yield.

IR: $\nu_{max}^{Nujol}$ 1590 cm$^{-1}$.

TLC: Rf=0.39 (Kiesel Gel 60 F$_{254}$ by Merck; i—C$_3$H$_7$OH:NH$_4$OH:CHCl$_3$=2:1:1).

The above powder (322 mg) is dissolved in an aqueous dilute ammonium hydroxide, and the resulting solution is treated with active carbon and evaporated under reduced pressure to yield 237 mg of pure 2-hydroxy-2-(1-diphenylmethylazetidin-3-yl)acetic acid.

EXAMPLE 2

Preparation of 1-N-[α-hydroxy-α-(azetidin-3-yl)acetyl] tobramycin sulfate

To a solution of 300 mg (0.502 mmole) of 3,2',6',3''-tetra-N-formyltobramycin, 179 mg (1.2 equivalents) of 2-hydroxy-2-(1-diphenylmethylazetidin-3-yl)acetic acid and 71 mg (1.2 equivalents) of N-hydroxysuccinimide in 2 ml of dimethylformamide is added 145 mg (1.4 equivalents) of dicyclohexylcarbodiimide, and the mixture is stirred at room temperature for 3 days. Dicyclohexylurea, which appears, is filtered off and washed with a small amount of dimethylformamide. The combined filtrate and washings are mixed with 70 ml of ethyl acetate. The precipitate, which appears, is collected by filtration, washed with ethyl acetate and dissolved in water. The resulting solution is evaporated under reduced pressure to yield 322 mg of 1-N-[2-hydroxy-2-(1-diphenylmethylazetidin-3-yl)acetyl]-3,2',6',3''-tetra-N-formyltobramycin as crude powder.

To a solution of the above product in 0.7 ml of water is added 4.2 ml of a mixture of concentrated hydrochloric acid (11 ml) and methanol (54.5 ml), and the mixture is stirred at 35° C. for 24 hours, diluted with water, and neutralized with 13 ml of Amberlite IR-45. The resin is filtered off and washed with water. The combined filtrate and washings are evaporated under reduced pressure to yield 308 mg of the residue, which is adsorbed on a column of silica gel (Kiesel gel 60 by Merck Co.) and eluted with a mixture of isopropanol, ammonium hydroxide and chloroform (5:1:1)(one fraction: 10 ml). Fraction Nos. 15 to 43 are evaporated under reduced pressure. The residue is readsorbed on a column of 8 ml of Amberlite CG-50 (NH$_4^+$) and after washing of the column with 50 ml of water, eluted with 150 ml of water and 150 ml of 0.4% ammonium hydroxide by gradient method (one fraction: 4 ml). Fraction Nos. 45 to 65 are evaporated under reduced pressure to yield 54 mg of 1-N-[2-hydroxy-2-(1-diphenylmethylazetidin-3-yl)acetyl]tobramycin.

The above product is dissolved in a mixture of 4 ml of water and 4 ml of dioxane and catalytically hydrogenated in the presence of 60 mg of 10% palladium-charcoal under hydrogen atmosphere at room temperature overnight. The catalyst is filtered off and washed with water. The combined filtrate and washings are evaporated under reduced pressure to yield 45 mg of the residue, which is adsorbed on a column of 4.5 ml of Amberlite CG-50 (NH$_4^+$) and after washing of the column with 50 ml of water, eluted with 100 ml of water and 200 ml of 1 N ammonium hydroxide by gradient method (one fraction: 2 ml). Fraction Nos. 91 to 131 are evaporated under reduced pressure. The residue is dissolved in water, treated with active carbon and evaporated to dryness under reduced pressure to yield 37 mg of 1-N-[2-hydroxy-2-(azetidin-3-yl)acetyl]tobramycin.

The above product is dissolved in 5 ml of water, adjusted to pH 4.6 with 2 ml of 0.1003 N sulfuric acid, mixed with 25 ml of ethanol, and somewhat concentrated under reduced pressure. The precipitate, which appears, is collected by filtration, washed with ethanol, and dissolved in water. The resulting solution is treated with active carbon and evaporated under reduced pressure to yield 36 mg of the residue. A part of the above residue (33.9 mg) is allowed to absorb moisture until the weight becomes constant, and 36 mg of 1-N-[2-hydroxy-2-(azetidin-3-yl)acetyl]tobramycin 2.5H$_2$SO$_4$.10H$_2$O is obtained in 5% overall yield.

$[\alpha]_D^{26.0}$+68.4°±1.1° (c=1.025, H$_2$O).

Elemental Analysis (for C$_{23}$H$_{44}$N$_6$O$_{11}$.2.5H$_2$SO$_4$.10H$_2$O): Calcd(%): C, 27.46; H, 6.91; N, 8.35; S, 7.97. Found(%): C, 27.11; H, 6.28; N, 8.38; S, 8.37.

EXAMPLE 3

Preparation of 2-hydroxy-2-(1-benzyloxycarbonylpyrrolidin-2-yl)acetic acid (1) To a solution of 3.40 g (3.21 mmoles) of 2-hydroxymethylpyrrolidine [prepared in the manner described in J. O. C. 32, 2388 (1967) by P. G. Gassman and A. Fentiman] in a mixture of 20 ml of acetone and 4 ml of water are dropwise added 5.0 ml (1.34 equivalents) of benzoyl chloride and 10 ml of an aqueous solution of 4.5 g (1.34 equivalents) of sodium carbonate at the same time and after 30 minutes, water is added thereto. The mixture is extracted with methylene chloride. The organic layer is separated, washed with water, dried over sodium sulfate and evaporated under reduced pressure to yield 8.4 g of the residue, which is adsorbed on a column of 84 g of Kiesel Gel 60 (prepared by Merck Co.) and eluted with benzene, a mixture of benzene and chloroform, and chloroform, successively. The eluate is evaporated under reduced pressure to yield 5.1 g of oily 1-benzoyl-2-hydroxymethylpyrrolidine in 77.5% yield.

IR: $\nu_{max}^{film}$ 3400, 1615, 1607, 1575, 1500 cm$^{-1}$.

(2) To a solution of 5.1 g (24.9 mmoles) of 1-benzoyl-2-hydroxymethylpyrrolidine in 70 ml of dry dimethylsulfoxide are 800 mg (8.2 mmoles) of orthophosphoric acid and 10.50 g (51 mmoles) of dicyclohexylcarbodiimide, and the mixture is stirred at room temperature, allowed to stand overnight, and mixed with 200 ml of ethyl acetate. Dicyclohexylurea, which appears, is filtered off, and the filtrate is mixed with water and extracted six times with ethyl acetate. The extract is washed thrice with water, dried over sodium sulfate, and evaporated under reduced pressure to yield 6.3 g of the oily residue, which is dissolved in benzene and washed with 23 (w/w) % aqueous sodium sulfite solution and twice with 18 (w/w) % aqueous sodium sulfite solution. The washings are neutralized with 100 ml of 23 (w/w) % aqueous sodium carbonate solution and reextracted four times with methylene chloride. The extract is dried over sodium sulfate and evaporated under reduced pressure to yield 3.210 g of 1-benzoyl-2-formylpyrrolidine in 63.5% yield.

IR: $\nu_{max}^{CHCl_3}$ 1737, 1600, 1580, 1500 cm$^{-1}$.

$[\alpha]_D^{24.5}$ −109.2°±1.5° (c=0.999, CHCl$_3$).

(3) To a solution of 3.347 g (16.5 mmoles) of 1-benzoyl-2-formylpyrrolidine in a mixture of 28 ml of tetrahydrofuran and 19 ml of water are added 1.30 g (20 mmoles; 1.23 equivalents) of potassium cyanide and 1.4 ml (16.7 mmoles) of concentrated hydrochloric acid. After 1 hour, the mixture is diluted with water and extracted with chloroform. The organic layer is separated, washed with water, dried over sodium sulfate, and evaporated under reduced pressure to yield 3.8 g of crude crystalline 2-hydroxy-2-(1-benzoylpyrrolidin-2-yl)acetonitrile in quantitative yield.

A part of the above crystals are recrystallized twice from a mixture of methylene chloride and hexane to yield needles having mp. 122° C. to 136° C.

IR: $\nu_{max}^{Nujol}$ 3265, 1611, 1600, 1574, 1501 cm$^{-1}$.

Elemental Analysis (for C$_{13}$H$_{14}$N$_2$O$_2$): Calcd(%): C, 67.81; H, 6.13; N, 12.17. Found (%): C, 68.08; H, 6.18; N, 12.02.

$[\alpha]_D^{24.5}$ −208.3°±2.4° (c=1.042, CHCl$_3$).

(4) A solution of 3.8 g (16.5 mmoles) of crude 2-hydroxy-2-(1-benzoylpyrrolidin-2-yl)acetonitrile in 30 ml of concentrated hydrochloric acid is refluxed for 1.5 hours, diluted with water, and washed with ether. The aqueous layer is adsorbed on a column of 100 ml of Amberlite IR-120B (H$^+$), washed with 300 ml of water and eluted with 500 ml of 5 N ammonium hydroxide. The eluate is evaporated under reduced pressure to yield the residue, which is dissolved in water. The resulting solution is treated with active carbon and concentrated under reduced pressure. The precipitate, which appears, is collected by filtration and washed with acetone to yield 1.102 g of 2-hydroxy-2-(pyrrolidin-2-yl)acetic acid as flaky crystals in 45.9% yield.

IR: $\nu_{max}^{Nujol}$ 3600–2000, 1657, 1625, 1585 cm$^{-1}$.

$[\alpha]_D^{24.5}$ −12.4°±0.5° (c=1.030, H$_2$O).

Elemental Analysis (for C$_6$H$_{11}$NO$_3$.1/5 H$_2$O): Calcd(%): C, 48.44; H, 7.72; N, 9.41. Found(%): C, 48.32; H, 7.80; N, 9.21.

(5) To a solution of 1.002 g (6.9 mmoles) of 2-hydroxy-2-(pyrrolidin-2-yl)acetic acid in a solution of 550 mg (2 equivalents) of sodium hydroxide in 10 ml of water is added 1.18 ml (1.2 equivalents) of benzyloxycarbonyl chloride, and the mixture is stirred at room temperature for 1.5 hours, washed twice with ether, adjusted to pH 2 with 10% hydrochloric acid, and then extracted thrice with methylene chloride. The extract is washed with water, dried over sodium sulfate and evaporated under reduced pressure to yield 1.288 g of α-hydroxy-α-(1-benzyloxycarbonylpyrrolidin-2-yl)acetic acid in 70.3% yield.

IR: $\nu_{max}^{CHCl_3}$ 3600–2300, 1715, 1695, 1500 cm$^{-1}$.

$[\alpha]_D^{25.5}$ −14.2°±0.6° (c=0.956, CHCl$_3$).

EXAMPLE 4

Preparation of 1-N-[2-hydroxy-2-(pyrrolidin-2-yl)acetyl]tobramycin sulfate

A solution of 578 mg (1.47 equivalents) of 2-hydroxy-2-(1-benzyloxycarbonylpyrrolidin-2-yl)acetic acid, 180 mg (1.1 equivalents) of N-hydroxysuccinimide, 379 mg (1.3 equivalents) of dicyclohexylcarbodiimide and 840 mg (1.41 mmoles) of 3,2′,6′,3″-tetra-N-formyltobramycin in 22 ml of dimethylformamide is allowed to stand overnight. Dicyclohexylurea, which appears, is filtered off and washed with 3 ml of dimethylformamide. The combined filtrate and washings are mixed with 250 ml of ethyl acetate. The insoluble materials are colloected by filtration, washed with ethyl acetate, and dissolved in water containing methanol. The resulting solution is evaporated under reduced pressure to yield 1.183 g of 1-N-[2-hydroxy-2-(1-benzyloxycarbonylpyrrolidin-2-yl) acetyl]-3,2′,6′,3″-tetra-N-formyltobramycin.

The above product is dissolved in 27 ml of a mixture of methanol and water (4:5) and catalytically hydrogenated in the presence of 414 mg of 10% palladium-charcoal under hydrogen atmosphere for 1 hour. The catalyst is filtered off and washed with methanol aqueous solution. The combined filtrate and washings are evaporated under reduced pressure to yield 1.032 g of 1-N-[2-hydroxy-2-(pyrrolidin-2-yl)acetyl]-3,2′,6′,3″-tetra-N-formyltobramycin.

The above product is dissolved in 1.71 ml of water, and 13.5 ml of a mixture of concentrated hydrochloric acid (11.0 ml) and methanol (54.5 ml) is added thereto. The mixture is warmed to 36° C. for 24 hours and neutralized with Amberlite IR-45. The resin is filtered off and washed with water. The combined filtrate and washings are evaporated under reduced pressure to yield 1.166 g of the residue, which is dissolved in 16 ml of water. The resulting solution is adsorbed on a column of 320 ml of Amberlite CG-50 (NH$_4^+$) and after washing of the column with 1.2 L of water, eluted with 1 L of water and 1 L of 1 N ammonium hydroxide by gradient method (one fraction: 15 ml). Fraction Nos. 79 to 86, 87 to 91, and 95 to 103 are respectively collected.

Fractions 95 to 103 are adjusted to pH 4.5 with 0.0955 N sulfuric acid, concentrated to 1 to 2 ml under reduced pressure, mixed with 50 ml of ethanol and cooled with ice. The precipitate, which appears, is collected by filtration, washed with ethanol, and dissolved in water. The resulting solution is treated with active carbon and lyophilized. The lyophilizate is allowed to absorb moisture until the weight becomes constant and 386 mg of 1-N-[2-hydroxy-2-(pyrrolidin-2-yl)acetyl]tobramycin 2.5H$_2$SO$_4$.9H$_2$O in 27.4% yield.

$[\alpha]_D^{25.0}$ +61.9°±1.0° (c=0.978, H$_2$O).

Elemental Analysis (for C$_{24}$H$_{46}$N$_6$O$_{11}$.2.5H$_2$SO$_4$.9H$_2$O): Calcd(%): C, 28.76; H, 6.94; N, 8.39; S, 8.00. Found(%): C, 29.00; H, 7.03; N, 8.29; S, 8.35.

NMR: $\delta_{ppm}^{D_2O}$ 6.42 (d, J=3.5 Hz), 5.75 (dd, J=2.5 Hz), 5.10 (d, J=5 Hz).

Fraction Nos. 79 to 86 are adsorbed on a column of 100 ml of Amberlite CG-50 (NH$_4^+$) and eluted with 1 L of water and 1 L of ammonium hydroxide (one fraction: 12 ml). Fraction Nos. 69 to 73 and 77 to 81 are collected respectively.

Fraction Nos. 77 to 81 and the aforementioned fraction Nos. 87 to 91 are combined, adjusted to pH 4.6 with 9.8 ml of 0.0955 N sulfuric acid, concentrated to 1 to 2 ml under reduced pressure, mixed with 50 ml of ethanol and cooled with ice. The precipitate, which appears, is collected by filtration, washed with ethanol, dissolved in water, treated with active carbon and lyophilized. The lyophilizate is allowed to absorb moisture until the weight becomes constant to yield 196 mg of 1-N-[2-hydroxy-2-(pyrrolidin-2-yl)acetyl]tobramycin 2.5H$_2$SO$_4$.9H$_2$O in 14% yield.

$[\alpha]_D^{25}$+76.4°±12° (c=1.011, H$_2$O).

Elemental Analysis (for C$_{24}$H$_{46}$N$_6$O$_{11}$.2.5H$_2$SO$_4$.9-H$_2$O): Calcd(%): C, 28.76; H, 6.94; N, 8.39; S, 8.00. Found(%): C, 29.04; H, 6.91; N, 8.32; S, 8.06.

NMR: $\delta_{ppm}^{D2O}$ 6.41 (d, J=3.5 Hz), 5.72 (d, J=3.0 Hz), 4.97 (d, J=4.5 Hz).

Fraction Nos. 69 to 73 are adjusted to pH 4.6 with 7.0 ml of 0.0955 N sulfuric acid, concentrated to 1 to 2 ml under reduced pressure, mixed with 50 ml of ethanol and cooled with ice. Precipitate, which appears, is collected by filtration, washed with ethanol, and dissolved in water. The resulting solution is treated with active carbon and lyophilized. The lyophilizate is allowed to absorb moisture until the weight becomes constant and 142 mg of 1-N-[2-hydroxy-2-(pyrrolidin-2-yl)acetyl]tobramycin 2.5H$_2$SO$_4$.9H$_2$O in 10.1% yield.

$[\alpha]_D^{25}$+60.7°±1.0° (c=1.014, H$_2$O).

Elemental Analysis (for C$_{24}$H$_{46}$N$_6$O$_{11}$.2.5H$_2$SO$_4$.9-H$_2$O): Calcd(%): C, 28.76; H, 6.94; N, 8.39; S, 8.00. Found(%): C, 29.08; H, 6.96; N, 8.25; S, 8.12.

NMR: $\delta_{ppm}^{D2O}$ 6.37 (d, J=3.5 Hz), 5.73 (d, J=3.0 Hz), 4.93 (d, J=5.8 Hz).

Total yield: 51.5%

EXAMPLE 5

Preparation of 2-hydroxy-2-(1-benzylpyrrolidin-3-yl) acetic acid (1) To a solution of 61.8 g (0.3 mole) of dicyclohexylcarbodiimide in 400 ml of dry dimethylsulfoxide is dropwise added a solution of 19.10 g (0.1 mole) of 1-benzyl-3-hydroxymethylpyrrolidine [prepared in the manner described in J. O. C. 26, 1519 (1961) by YAO-HUA WU and R. F Feldkamp] under ice-cooling for 15 minutes, and the mixture is stirred at room temperature overnight. Dicyclohexylcarbodiimide (13.26 g; 60 mmoles) and phosphorus pentachloride (4.40 g; 30 mmoles) are added thereto and the mixture is stirred overnight, poured into ice water, mixed with 300 ml of methylene chloride and stirred for 30 minutes. The insoluble materials, which appear, are filtered off and washed with water. The combined filtrate and washings are washed twice with 200 ml of methylene chloride, adjusted to pH 9 with 20 (w/w) % aqueous sodium carbonate solution, and extracted four times with 200 ml of methylene chloride. The extract is washed with 20 (w/w) % aqueous sodium hydrogensulfite solution. The aqueous layer is separated, washed thrice with 100 ml of methylene chloride, mixed with 20 (w/w) % aqueous sodium carbonate solution, and extracted with methylene chloride. The extract is washed with water, dried over sodium sulfate and evaporated under reduced pressure to yield crude oily 1-benzyl-3-formylpyrrolidine in 66% yield.

(2) To a solution of 12.45 g of crude 1-benzyl-3-formylpyrrolidine in a mixture of 23 ml of tetrahydrofuran and 23 ml of water is added 11.4 ml (2 equivalents) of concentrated hydrochloric acid and then 8.39 g (2 equivalents) of potassium cyanide powder in a period of 15 minutes under ice-cooling. The mixture is stirred at the same temperature for 2 hours, adjusted to pH 10 with 10% aqueous sodium carbonate solution, and extracted thrice with methylene chloride. The extract is washed with water, dried over sodium sulfate and evaporated under reduced pressure to yield 12.05 g of 2-hydroxy-2-(1-benzylpyrrolidin-3-yl) acetonitrile.

(3) A solution of 12.05 g of 2-hydroxy-2-(1-benzylpyrrolidin-3-yl)acetonitrile in 23 ml of concentrated hydrochloric acid is heated on a bath for 1 hour and allowed to stand overnight. After cooling, precipitated ammonium chloride is filtered off and washed with acetone. The combined filtrate and washings are evaporated under reduced pressure to yield the residue, which is dissolved in water, mixed with 20 ml of 23 (w/w) % aqueous sodium hydroxide solution and washed with methylene chloride. The aqueous layer is slowly adsorbed on a column of 300 ml of Amberlite IR-120B(H$^+$) and after washing of the column with water, eluted with 1 N ammonium hydroxide. The eluate is evaporated to dryness under reduced pressure, and the residue is mixed with acetone. The precipitate, which appears, is collected by filtration and recrystallized from a mixture of ethanol and acetone to yield 1.422 g of 2-hydroxy-2-(1-benzylpyrrolidin-3-yl)acetic acid. mp. 174° to 176° C.

IR: $\nu_{max}^{Nujol}$ 3400–2200, 1619 cm$^{-1}$.

Elemental Analysis (for C$_{13}$H$_{17}$NO$_3$) Calcd(%): C, 66.39; H, 7.28; N, 5.95. Found(%): C, 66.09; H, 7.27; N, 5.72.

The mother liquor (3.4 g) is chromatographed on a column of 360 g of Kiesel Gel 60 (prepared by Merck Co.) and eluted with a mixture of isopropanol and concentrated ammonium hydroxide (30:1). The eluate is evaporated to dryness under reduced pressure, and the residue is crystallized from ethanol to yield 2.70 g of 2-hydroxy-2-(1-benzylpyrrolidin-3-yl)acetic acid.

Total Yield: 4.122 g (17.5%).

EXAMPLE 6

Preparation of 1-N-[2-hydroxy-2-(pyrrolidin-3-yl)acetyl]tobramycin sulfate

To a solution of 598 mg (1.0 mmole) of 3,2',6',3''-tetra-N-formyltobramycin in 15 ml of dimethylformamide are added 449 mg (1.9 equivalents) of 2-hydroxy-2-(1-benzylpyrrolidin-3-yl)acetic acid, 219 mg (1.9 equivalents) of N-hydroxysuccinimide and 392 mg (1.9 equivalents) of dicyclohexylcarbodiimide, and the mixture is stirred at 50° C. on an oil bath for 10 hours and cooled. Dicyclohexylurea, which appears, is filtered off and washed with a small amount of dimethylformamide. The combined filtrate and washings are mixed with 300 ml of ethyl acetate. The precipitate, which appears, is collected by filtration, washed with ethyl acetate, and dissolved in water. The resulting solution is evaporated to dryness under reduced pressure.

To a solution of the above residue in 1.5 ml of water is added 10 ml of a mixture of concentrated hydrochloric acid (11.0 ml) and methanol (54.5 ml), and the mixture is stirred at 37° C. for 24 hours and neutralized with 25 ml of Amberlite IR-45. The resin is filtered off and washed with water. The combined filtrate and washings are evaporated under reduced pressure to yield the residue, which is dissolved in a small amount of water, adsorbed on 160 ml of a column of Amberlite CG-50 (NH$_4^+$), and after washing of the column with 400 ml of water, eluted with 0.2% aqueous ammonium hydroxide (one fraction: 16 ml) until Fraction No. 161 and then with 0.3% aqueous ammonium hydroxide solution from Fraction No. 162. Fraction Nos. 182 to 199 are collected and evaporated. The residue (400 mg) is dissolved in 24 ml of 50% methanol and catalytically hydrogenated in the presence of 260 mg of 10% palladium-charcoal under hydrogen atmosphere overnight. The catalyst is filtered off and washed with aqueous methanol. The combined filtrate and washings are evaporated under reduced pressure.

The above residue (384 mg) is dissolved in a small amount of water, adsorbed on a column of 60 ml of Amberlite CG-50 ($NH_4^+$) and after washing of the column, eluted with 1 L of water and 1 L of 1 N ammonium hydroxide by gradient method (one fraction: 13 ml). Fraction Nos. 109 to 135 are concentrated under reduced pressure, treated with active carbon, filtered and evaporated under reduced pressure. The residue (301 mg) is adjusted to pH 4.65 with 21.6 ml of 0.0955 N sulfuric acid, concentrated to about 1 to 2 ml under reduced pressure and mixed with 40 ml of ethanol. The precipitate, which appears, is collected by filtration, washed with ethanol and dissolved in water. The resulting solution is treated with active carbon, and lyophilized.

The lyophilizate is allowed to absorb moisture until the weight becomes constant to yield 408.5 mg of 1-N-[2-hydroxy-2-(pyrrolidin-3-yl)acetyl]tobramycin sulfate in 41.6% yield.

$[\alpha]_D^{26} + 72.4 \pm 1.1°$ (c=1.036, $H_2O$).

Elemental Analysis (for $C_{24}H_{46}N_6O_{11} \cdot 2.5H_2SO_4 \cdot 8\text{-}H_2O$): Calcd(%): C, 29.29; H, 6.86; N, 8.54; S, 8.15. Found(%): C, 29.34; H, 6.98; N, 8.47; S, 8.23.

NMR: $\delta_{ppm}^{D_2O}$ 6.33 (d, J=3.5 Hz), 5.67 m.

EXAMPLE 7

Preparation of 2-hydroxy-2-(1-benzyloxycarbonylpiperidin-3-yl)acetic acid (1) A solution of 2-hydroxy-2-(piperidin-3-yl) acetic acid hydrochloride [prepared in the manner described in Archive der Pharmazie, 292, 38 (1959) by W. Sauermilch and A. Wolf] in a amixture of 10 ml of water and 15 ml of acetic acid is catalytically hydrogenated in the presence of platinum oxide monohydrate under hydrogen atmosphere overnight. The catalyst is filtered off and washed with water. The combined filtrate and washings are evaporated under reduced pressure. The residue is crystallized from acetone. The crystals are collected by filtration, washed with acetone, recrystallized from acetone to yield 2.151 g of 2-hydroxy-2-(piperidin-3-yl)acetic acid hydrochloride having mp. 185° C. to 188° C. in 78.5% yield. Further the crystals are recrystallized twice from acetone to yield the same product having 189° C. to 192° C. as microprisms.

IR: $\nu_{max}^{Nujol}$ 3246, 1722, 1627, 1570 $cm^{-1}$.

Elemental Analysis (for $C_7H_{13}NO_3 \cdot HCl$):
Calcd(%): C, 42.97; H, 7.21; N, 7.16; Cl, 18.13.
Found(%): C, 42.78; H, 7.29; N, 7.17; Cl, 18.20.

(2) To a solution of 2-hydroxy-2-(piperidin-3-yl)acetic acid hydrochloride (1.956 g; 10 mmoles) in 2.7 (w/w) % aqueous sodium hydroxide solution is added 1.72 ml (1.2 equivalents) of benzyloxycarbonylchloride. After 2 hours, the reaction mixture is washed twice with ether, adjusted to pH 1 to 2 with 10% hydrochloric acid, and extracted thrice with methylene chloride. The extract is washed with water, dried over sodium sulfate, and evaporated under reduced pressure to yield 2.650 g of oily 2-hydroxy-2-(1-benzyloxycarbonylpiperidin-3-yl) acetic acid in 90.4% yield.

IR: $\nu_{max}^{CHCl_3}$ 1724, 1686 $cm^{-1}$.

EXAMPLE 8

Preparation of 1-N-[2-hydroxy-2-(piperidin-3-yl)acetyl] tobramycin sulfate

To a solution of 299 mg (0.5 mmole) of 3,2',6', 3''-tetra-N-formyltobramycin in 5 ml of dimethylformamide are added 191 mg (1.3 equivalents) of 2-hydroxy-2-(1-benzyloxycarbonylpiperidin-3-yl)acetic acid, 75 mg (1.3 equivalents) of N-hydroxysuccinimide and 134 mg of dicyclohexylcarbodiimide, and the mixture is allowed to stand at room temperature for 3 days. Dicyclohexylurea, which appears, is filtered off and washed with a small amount of dimethylformamide. The combined filtrate and washings are mixed with 200 ml of ethyl acetate and cooled with ice. After 30 minutes, insoluble materials, which appear, are collected by filtration, washed with ethyl acetate and then dissolved in aqueous methanol. The resulting solution is evaporated under reduced pressure to yield 518 mg of 1-N-[2-hydroxy-2-(1-benzyloxycarbonylpiperidin-3-yl)acetyl]3,2',6',3''-tetra-N-formyltobramycin.

A solution of the above product is a mixture of 21.3 ml of water and 8.3 ml of methanol, is catalytically hydrogenated in the presence of 217 mg of 10% palladium-charcoal for 2.5 hours. The catalyst is filtered off and washed with water. The combined filtrate and washings are evaporated under reduced pressure to yield 381 mg of 1-N-[2-hydroxy-2-(piperidin-3-yl)acetyl]-3,2',6',3''-tetra-N-formyltobramycin.

To a solution of the above product in 0.5 ml of water is added 5 ml of a mixture of concentrated hydrochloric acid (11.0 ml) and methanol (54,5 ml), and the mixture is stirred at 36° C. for 24 hours, and neutralized with 13 ml of Amberlite IR-45. The resin is filtered off and washed with water. The combined filtrate and washings are evaporated under reduced pressure. The residue (390 mg) is dissolved in a small amount of water, adsorbed on a column of 120 ml of Amberlite CG-50 ($NH_4^+$) and after washing of the column with 500 ml of water, eluted with 1 L of water and 1 L of 1N ammonium hydroxide by gradient method (one fraction: 13 ml). Fraction Nos. 113 to 123 are evaporated under reduced pressure. The residue is dissolved in water, treated with active carbon, filtered and washed. The filtrate is evaporated under reduced pressure to yield 248 mg of 1-N-[2-hydroxy-2-(piperidin-3-yl)acetyl]tobramycin.

The above product is adjusted to pH 4.6 with 16.0 ml of 0.0955 N sulfuric acid, evaporated under reduced pressure, mixed with 40 ml of ethanol and cooled with ice. The precipitate, which appears, is collected by filtration, washed with ethanol and dissolved in water. The resulting solution is treated with active carbon, filtered and lyophilized. The lyophilizate is allowed to absorb moisture until the weight becomes constant and 316 mg of 1-N-[2-hydroxy-2-(piperidin-3-yl)acetyl]tobramycin $2.5H_2SO_4 \cdot 9H_2O$ is obtained in 62.2% yield.

$[\alpha]_D^{24.5} + 68.7 \pm 1.1°$ (c=1.002, $H_2O$).

Elemental Analysis (for $C_{25}H_{48}N_6O_{11} \cdot 2.5H_2SO_4 \cdot 9H_2O$).
Calcd(%): C,29.55; H, 7.04; N, 8.27; S, 7.89.
Found (%): C, 29.78; H, 7.07; N, 8.04; S, 7.83.
NMR: $\delta_{ppm}^{CDCl_3}$ 6.34 (d, J=3.5Hz), 5.67m.

EXAMPLE 9

Preparation of 2-hydroxy-2-(1,4-dibenzylpiperazin-2-yl) acetic acid (1) To a solution of 5.0 g (13.9 mmoles) of ethyl 1,4-dibenzylpiperazin-2-carboxylate [prepared in the manner described in Helv. Chim. Acta, 298, 2646(1963) by E. Jucker and E. Rissi] in 40 ml of dry ether is dropwise added 30 ml of a solution of 1.46 moles of diisobutylaluminium hydride in toluene at $-56°$ to $-66°$ C. under nitrogen atmosphere in a period of 15 minutes, and the mixture is stirred at the same temperature for 1 hour. 10% Aqueous sodium hydroxide solution (20 ml) is slowly dropwise added thereto, and the mixture is warmed up to room temperature and extracted with ether. The extract is washed with water, dried over magnesium sulfate and evaporated under reduced pressure to yield 5.2 g of crude 1,4-dibenzyl-2-formylpiperazine.

IR: $\nu_{max}^{CHCl_3}$ 1725 cm$^{-1}$.

(2) To a solution of 5.2 g of crude 1,4-dibenzyl-2-formylpiperazine in a mixture of 30 ml of tetrahydrofuran and 10 ml of water are added 2.2 g (33.8 mmoles) of potassium cyanide and 3.4 ml of concentrated hydrochloric acid under ice-cooling, and the mixture is stirred for 30 minutes, mixed with water and extracted with chloroform. The extract is washed with water, dried over magnesium sulfate and evaporated under reduced pressure to yield 5.70 g of crude oily 2-hydroxy-2-(1,4-dibenzylpiperazin-2-yl)acetonitrile.

(3) A solution of 5.70 g of crude 2-hydroxy-2-(1,4-dibenzylpiperazin-2-yl)acetonitrile in 9.2 ml of concentrated hydrochloric acid is warmed on a bath for 1 hour. After cooling, the solution is alkalified with 13 (w/w) % aqueous sodium hydroxide solution, washed with methylene chloride, adsorbed on a column of 280 ml of Amberlite IR-120B(H+) and after washing of the column with 2.5 L of water, eluted with 1 N aqueous ammonium hydroxide solution. The eluate is concentrated under reduced pressure to yield 2.8 g of the viscose residue, which is dissolved in a mixture of 25 ml of water and 2.5 ml of isopropanol, adsorbed on a column of Kiesel gel 60 (prepared by Merck) and eluted with isopropanol-concentrated ammonium hydroxide (4:1) (one fraction: 16 g). Fraction Nos. 12 to 20 are collected and evaporated under reduced pressure. The residue is dissolved in water, treated with active carbon and filtered. The filtrate is evaporated under reduced pressure to yield 2.239 g of 2-hydroxy-2-(1,4-dibenzylpiperazin-2-yl)acetic acid in 47% yield.

IR: $\nu_{max}^{CHCl_3}$ 1635 cm$^{-1}$.

(4) To a solution of 452 mg of 2-hydroxy-2-(1,4-dibenzylpiperazin-2-yl)acetic acid in 5 ml of methanol is added a solution of diazomethane in ether. After the excess amount of diazomethane is decomposed with acetic acid, the mixture is evaporated to dryness under reduced pressure. The residue is dissolved in ether. The resulting solution is washed with 10% aqueous sodium sulfate and water, dried over sodium sulfate and evaporated under reduced pressure to yield 468 mg of methyl 2-hydroxy-2-(1,4-dibenzylpiperazin-2-yl)acetate as a mixture of erythro and threo.

(5) The above product (2.1 g) is separated and purified by means of liquid chromatography [prepack column, size c; benzene-ethyl acetate (7:3)] to yield 912 mg of less polar ester, 896 mg of more polar ester and 40 mg of their mixture. The yield is respectively 43.4%, 42.7% and 2%.

(6) To a solution of 632 mg (1.86 mmoles) of the above less polar product in 3 ml of methanol are added 256 mg (3.9 mmoles) of 86% potassium hydroxide and 0.5 ml of water, and the mixture is allowed to stand at room temperature overnight and evaporated under reduced pressure. The residue is dissolved in water, slowly adsorbed on a column of 80 ml of Amberlite IR-120B (H+) and after washing of the column with 500 ml of water, eluted with 1 N aqueous ammonium hydroxide solution. The eluate is evaporated under reduced pressure to yield the residue, which is dissolved in water. The resulting solution is treated with active carbon and filtered. The filtrate is evaporated under reduced pressure to yield 590 mg of viscose 2-hydroxy-2-(1,4-dibenzylpiperazin-2-yl)acetic acid (less polar isomer) in 97% yield.

IR: $\nu_{max}^{CHCl_3}$ 3400, 1600 cm$^{-1}$.

(7) To a solution of 687 mg (1.85 mmoles) of the more polar product prepared in the above (5) in 3 ml of methanol are added 242 mg (3.71 mmoles) of 86% potassium hydroxide and 0.5 ml of water, and the mixture is allowed to stand overnight and evaporated under reduced pressure. The residue is dissolved in water, slowly adsorbed on 80 ml of Amberlite IR-120B (H+) and after washing of the column with 500 ml of water, eluted with 1 N aqueous ammonium hydroxide. The eluate is evaporated under reduced pressure to yield the residue, which is dissolved in water. The resulting solution is treated with active carbon and filtered. The filtrate is concentrated under reduced pressure to yield 622 mg of 2-hydroxy-2-(1,4-dibenzylpiperazin-2-yl)acetic acid as more polar product in 93% yield.

IR: $\nu_{max}^{CHCl_3}$ 3400, 1621 cm$^{-1}$.

EXAMPLE 10

Preparation of 1-N-[2-hydroxy-2-(piperazin-2-yl)acetyl] tobramycin sulfate (1) To a solution of 234 mg (1.4 equivalents) of 2-hydroxy-2-(1,4-dibenzylpiperazin-2-yl)acetic acid (less polar isomer) prepared in Example 9-(6) in 6 ml of dimethylformamide are added 144 mg (1.4 equivalents) of dicyclohexylcarbodiimide, 80 mg (1.4 equivalents) of N-hydroxysuccinimide and 300 mg (0.5 mmole) of 3,2',6',3''-tetra-N-formyltobramycin, and the mixture is allowed to stand at room temperature overnight. Dicyclohexylurea, which appears, is filtered off and washed with a small amount of dimethylformamide. The combined filtrate and washings are concentrated to 1 to 2 ml under reduced pressure and mixed with 50 ml of ethyl acetate. The precipitate, which appears, is washed with ethyl acetate and dissolved in water. The resulting solution is evaporated under reduced pressure to yield 419 mg of 1-N-[2-hydroxy-2-(1,4-dibenzylpiperazin-2-yl)acetyl]-3,2',6',3''-tetra-N-formyltobramycin.

To a solution of the above product in 0.63 ml of water is added 5 ml of a mixture of concentrated hydrochloric acid (11.0ml) and methanol (54.5 ml), and the mixture is stirred at 35° to 37° C. on an oil bath for 24 hours, and neutralized with 30 ml of Amberlite IR-45. The resin is filtered off and washed with water. The combined filtrate and washings are evaporated under reduced pressure. The residue (463 mg) is dissolved in a mixture of 1 ml of water and 1 ml of isopropanol, slowly adsorbed on a column of 50 g of Kiesel gel 60 (prepared by Merck Co.) and eluted with a mixture of isopropanol, concentrated ammonium hydroxide and chloroform (4:1:1)

(one fraction: 10 ml). Fraction Nos. 12 to 24 are evaporated under reduced pressure. The residue is dissolved in water, treated with active carbon, and filtered. The filtrate is evaporated under reduced pressure to yield 260 mg of 1-N-[2-hydroxy-2-(1,4-dibenzylpiperazin-2-yl)acetyl]tobramycin.

The above product is dissolved in a mixture of 2 ml of water and 2 ml of acetic acid, and catalytically hydrogenated in the presence of 127 mg of 10% palladium-charcoal under hydrogen atmosphere at high atmospheric pressure of 4 atoms. The catalyst is filtered off and washed with water. The combined filtrate and washings are evaporated under reduced pressure. The residue (276 mg) is dissolved in a small amount of water, slowly adsorbed on a column of 60 ml of Amberlite CG-50 (NH$_4$+) and after washing of the column with 1 L of water, eluted with a mixture of 1 L of water and 1 L of aqueous ammonium hydroxide by gradient method (one fraction: 15 ml). Fraction Nos. 48 to 56 are evaporated under reduced pressure. The residue is dissolved in water, treated with active carbon, filtered and washed with water. The filtrate is concentrated under reduced pressure to yield 134 mg of 1-N-[2-hydroxy-2-(piperazine-2-yl)acetyl]tobramycin.

The above product is adjusted to pH 4.5 with 9.4 ml of 0.0966 N sulfuric acid, concentrated to about 1 to 2 ml under reduced pressure, and mixed with 50 ml of ethanol. The precipitate, which appears, is collected by filtration, washed with ethanol, dissolved in water, treated with active carbon, and filtered. The filtrate is lyophilized and the lyophilizate is allowed to absorb moisture to yield 188 mg of 1-N-[2-hydroxy-2-(piperazin-2-yl)acetyl]tobramycin 2.5H$_2$SO$_4$.10H$_2$O in 36.2% yield. $[\alpha]_D^{26} + 67.1 \pm 1.0°$ (c=1.048, H$_2$O).

Elemental Analysis (for C$_{24}$H$_{46}$N$_7$O$_{11}$.2.5H$_2$SO$_4$.10H$_2$O): Calcd(%): C, 27.88; H, 6.92; N, 9.48; S, 7.75. Found(%): C, 27.69; H, 6.68; N, 9.40; S, 8.00.

NMR: $\delta_{ppm}^{D_2O}$ 6.37 (d, J=4.0Hz), 5.67 m.

(2) To a solution of 327 mg (1.4 equivalents) of 2-hydroxy-2-(1,4-dibenzylpiperazin-2-yl)acetic acid (more polar) in 6 ml of dimethylformamide are added 193 mg (1.4 equivalents) of dicyclohexylcarbodiimide, 108 mg (1.4 equivalents) of N-hydroxysuccinimide and 400 mg (0.67 mmole) of 3,2′,6′,3″-tetra-N-formyltobramycin, and the mixture is allowed to stand at room temperature overnight. Dicyclohexylurea, which appears, is filtered off and washed with a small amount of dimethylformamide. The combined filtrate and washings are concentrated to about 1 to 2 ml under reduced pressure and mixed with 50 ml of ethyl acetate. The precipitate, which appears, is washed with ethyl acetate, dissolved in water, and evaporated under reduced pressure to yield 541 mg of 1-N-[2-hydroxy-2-(1,4-dibenzylpiperazin-2-yl)acetyl]3,2′,6′,3″-tetra-N-formyltobramycin.

To a solution of the above product in 0.85 ml of water is added 6.7 ml of a mixture of concentrated hydrochloric acid (11.0 ml) and methanol (54.5 ml), and the mixture is stirred at 35° C. to 37° C. on an oil bath for 24 hours and neutralized with 30 ml of Amberlite IR-45. The resin is filtered off and washed with water. The combined filtrate and washings are evaporated under reduced pressure. The residue (544 mg) is dissolved in a mixture of 1 ml of water and 1 ml of isopropanol, slowly adsorbed on a column of 70 g of Kiesel gel 60 (prepared by Merck Co.) and eluted with a mixture of isopropanol, concentrated ammonium hydroxide and chloroform (2:1:1) (one fraction: 15 ml). Fractions 23 to 38 are evaporated under reduced pressure. The residue is dissolved in water, treated with active carbon, and filtered. The filtrate is evaporated under reduced pressure to yield 337 mg of 1-N-[2-hydroxy-2-(1,4-dibenzylpiperazin-2-yl)acetyl]tobramycin.

The above product is dissolved in a mixture of 3 ml of water and 3 ml of acetic acid and catalytically hydrogenated in the presence of 10% palladium-charcoal at high pressure of 4 atoms in hydrogen atmosphere. The catalyst is filtered off and washed with water. The combined filtrate and washings are evaporated under reduced pressure. The residue (311 mg) is dissolved in a small amount of water, slowly adsorbed on a column of 80 ml of Amberlite CG-50 (NH$_4$+) and after washing of the column, eluted with 1 L of water and 1 L of 1 N ammonium hydroxide by gradient method (one fraction: 18 ml). Fraction Nos. 47 to 56 are evaporated to dryness under reduced pressure. The residue is treated with active carbon, filtered, and washed with water. The filtrate is evaporated under reduced pressure to yield 178 mg of 1-N-[2-hydroxy-2-(piperazin-2-yl)acetyl]tobramycin.

The above product is adjusted to pH 4.5 with 13 ml of 0.0966 N sulfuric acid, evaporated under reduced pressure. The residue is mixed with 50 ml of ethanol. The precipitate, which appears, is washed with ethanol, dissolved in water, treated with active carbon, filtered and lyophilized. The lyophilizate is allowed to absorb moisture to yield 265 mg of 1-N-[2-hydroxy-2-(piperazin-2-yl)acetyl]tobramycin 2.8H$_2$SO$_4$.10H$_2$O in 37.3% yield. $[\alpha]_D^{25.5} + 69.9 \pm 1.1°$ (c=1.024, H$_2$O).

Elemental Analysis (for C$_{24}$H$_{46}$N$_7$O$_{11}$.2.8H$_2$SO$_4$.10H$_2$O): Calcd(%): C, 27.10; H, 6.80; N, 9.22; S, 8.44. Found(%): C, 27.29; H, 6.60; N, 9.31; S, 8.42.

NMR: $\delta_{ppm}^{D_2O}$ 6.38 (broad d, J=3.6Hz), 5.67 m.

EXAMPLE 11

Preparation of 2-hydroxy-2-(1-diphenylmethylazetidin-2-yl)acetic acid (1) To a suspension of 0.57 g of lithium aluminium hydride in 30 ml of dry ether is dropwise added a solution of 6 g (0.021 mole) of 1-diphenylmethyl-2-methoxycarbonylazetidine [prepared in the manner described in J. Heterocyclic Chem., 6, 435 (1969) by R. M. Rodebaugh and N. H. Cromwell] in 30 ml of dry ether in a period of 15 minutes, and the mixture is stirred at room temperature for 15 minutes. The excess amount of lithium aluminium hydride is decomposed with ethyl acetate. The insoluble materials are filtered off and washed with dry ether. The combined filtrate and washings are evaporated to dryness under reduced pressure. The residue is dissolved in ether and the resulting solution is evaporated to yield 4.7 g of crude syrupy 1-diphenylmethyl-2-hydroxymethylazetidine in 90% yield.

(2) To a solution of 2.36 g (17.7 mmoles) of N-chlorosuccinimide in 40 ml of dry toluene is added 1.77 ml (24.2 mmoles) of dimethyl sulfide, and the mixture is stirred at the same temperature for 25 minutes and cooled to −25° C. to −30° C. A solution of 3 g (11.8 mmoles) of 1-diphenylmethyl-2-hydroxymethylazetidine in 8 ml of toluene is dropwise added thereto in a period of 20 minutes and the mixture is stirred at the same temperature for 2 hours. A solution of 2.5 ml (11.8 mmoles) of triethylamine in 2 ml of toluene is dropwise added thereto in a period of 15 minutes. The reaction mixture is stirred at −25° C. for 30 minutes, mixed with 120 ml of ether, stirred at room temperature for 5 minutes, washed twice with 50 ml of water, dried over sodium sulfate and evaporated under reduced pressure. The resulting syrupy residue (3.2 g) is dissolved in 50 ml of methylene chloride and extracted four times with 20 (w/w) % aqueous sodium hydrogensulfite solution. The extract is washed with 20 ml of methylene chloride, adjusted to pH 10 with 20% aqueous sodium carbonate solution, and extracted four times with 50 ml of methylene chloride. The extract is washed with water, dried over sodium sulfate and evaporated under reduced pressure. The resulting syrupy residue (2.1 g) is recrystallized from a mixture of n-hexane and ether to yield 2 g of 1-diphenylmethyl-2-formylazetidine in 67% yield.

mp. 85° to 86° C.

IR: $\nu_{max}^{film}$ 1722 cm$^{-1}$.

Elemental Analysis (for $C_{17}H_{17}NO$): Calcd(%): C, 81.24; H, 6.82; N, 5.75. Found(%): C, 81.22; H, 6.79; N, 5.60.

(3) To a solution of 1.4 g (5.57 mmoles) of 1-diphenylmethyl-2-formylazetidine in a mixture of 7.5 ml of tetrahydrofuran and 7.5 ml of water is added 0.91 ml (11.14 mmoles) of concentrated hydrochloric acid under cooling and then 0.724 g (11.14 mmoles) of potassium cyanide is added thereto. The mixture is stirred for 2 hours and extracted with 30 ml of ether. The aqueous layer is reextracted with 30 ml of ether. The extract and the above organic layer are combined, washed with water, dried over magnesium sulfate and evaporated under reduced pressure to yield 1.6 g of crude syrupy 2-hydroxy-2-(1-diphenylmethylazetidin-2-yl)acetonitrile in quantitative yield.

IR: $\nu_{max}^{film}$ 2240 cm$^{-1}$.

(4) The above product (1.5 g; 5.4 mmoles) is dissolved in 2 ml of concentrated hydrochloric acid, and the resulting solution is stirred at 85° C. for 1 hour and evaporated under reduced pressure. The excess amount of concentrated hydrochloric acid is removed off by azeotropic distillation with water. The residue is dissolved in 50 ml of water containing 1 g of sodium hydroxide, and washed with 30 ml of chloroform. The washings are extracted with 30 ml of water containing 0.5 g of sodium hydroxide. The extract and the above solution are combined, slowly adsorbed on a column of 100 ml of IR-120B (H$^+$), and eluted with 1 L of 5 N aqueous ammonium hydroxide, after washing of the column with water until the washing becomes neutral. The eluate is concentrated under reduced pressure to yield 0.8 g of 2-hydroxy-2-(1-diphenylmethylazetidin-2-yl)acetic acid in 50% yield as powder.

IR: $\nu_{max}^{KBr}$ 1600 cm$^{-1}$.

Elemental Analysis (for $C_{18}H_{19}NO_3$): Calcd(%): C, 72.70; H, 6.44; N, 4.71. Found(%): C, 72.90; H, 6.54; N, 4.69.

EXAMPLE 12

Preparation of 1-N-[2-hydroxy-2-(azetidin-2-yl)acetyl]tobramycin sulfate

A solution of 300 mg (0.502 mmole) of 3,2',6',3''-tetra-N-formyltobramycin, 164 mg (1.1 equivalents) of 2-hydroxy-2-(1-diphenylmethylazetidin-2-yl)acetic acid, 64 mg (1.1 equivalents) of N-hydroxysuccinimide and 114 mg (1.1 equivalents) of dicyclohexylcarbodiimide in 2.5 ml of dimethylformamide is allowed to stand at room temperature for 16 hours. Dicyclohexylurea, which appears, is filtered off. The filtrate is mixed with 10 times amount of ethyl acetate. The precipitate, which appears, is collected by filtration and washed with methanol to yield 350 mg of 1-N-[2-hydroxy-2-(1-diphenylmethylazetidin-2-yl)acetyl]-3,2',6',3''-tetra-N-formyltobramycin. To a solution of the above product in 0.8 ml of water is added 6.8 ml of a mixture of concentrated hydrochloric acid (11.0 ml) and methanol (54.5 ml), and the mixture is stirred at 36° C. for 20 hours and neutralized with Amberlite IR-45 (OH$^-$). The resin is filtered off and the filtrate is concentrated under reduced pressure to yield 300 mg of 1-N-[2-hydroxy-2-(1-diphenylmethylazetidin-2-yl)acetyl]tobramycin.

The above product is dissolved in 15 ml of water and catalytically hydrogenated in the presence of 200 mg of 10% palladium - charcoal under hydrogen atmosphere for 20 hours. The catalyst is filtered off, and the filtrate is washed twice with 50 ml of ether and evaporated under reduced pressure. The residue (225 mg) is dissolved in 20 ml of water, adsorbed on a column of 30 ml of Amberlite CG-50 (NH$_4^+$), and after washing of the column with 100 ml of water, eluted with 1 N aqueous ammonium hydroxide (one fraction: 10 ml). Fraction Nos. 16 to 25 are evaporated under reduced pressure to yield 120 mg of 1-N-[2-hydroxy-2-(azetidin-2-yl)acetyl]tobramycin.

The above product is adjusted to pH 4.6 with 6.8 ml of 0.0955 N sulfuric acid, concentrated to 1 to 2 ml under reduced pressure, mixed with 50 ml of ethanol, and cooled with ice. The precipitate, which appears, is collected by filtration, washed with ethanol, and dissolved in water. The resulting solution is treated with active carbon and filtered. The filtrate is lyophilized and the lyophilizate is allowed to absorb moisture until the weight becomes constant and 125 mg of 1-N-[2-hydroxy-2-(azetidin-2-yl)acetyl]tobramycin 2.5H$_2$SO$_4$.9H$_2$O.

$[\alpha]_D^{25}$ +65.1±1.0° (c=1.014, H$_2$O).

Elemental Analysis (for $C_{23}H_{44}N_6O_{11}$.2.5H$_2$SO$_4$.9H$_2$O): Calcd(%): C, 27.96; H, 6.84; N, 8.51; S, 8.11. Found(%): C, 28.21; H, 6.67; N, 8.23; S, 8.25.

We claim:

1. A novel aminoglycoside derivative represented by the formula:

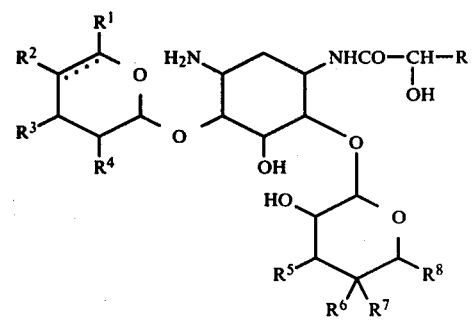

wherein

R is a member of the group consisting of 2-azetidinyl, 3-azetidinyl, 2-pyrrolyl, 3-pyrrolyl, 2-pyrrolinyl, 3-pyrrolinyl, 2-pyrrolidinyl, 3-pyrrolidinyl, 2-imidazolyl, 4-imidazolyl, 2-imidazolinyl, 4-imidazolinyl, 2-imidazolidinyl, 4-imidazolidinyl, 3-pyrazolyl, 4-pyrazolyl, 3-pyrazolinyl, 4-pyrazolinyl, 3-pyrazolidinyl, 4-pyrazolidinyl, 2-pyridyl, 3-pyridyl, 4-pyridyl, 2-piperidyl, 3-piperidyl, 4-piperidyl, 3-pyridazinyl, 4-pyridazinyl, 2-pyrimidinyl, 4-pyrimidinyl, 5-pyrimidinyl, 2-pyrazinyl, 3-pyrazinyl, 2-piperazinyl, and 3-piperazinyl;

$R^1$ is aminomethyl, hydroxymethyl, 1-aminoethyl, or 1-methylaminoethyl;

$R^2$, $R^3$ and $R^6$ each is hydrogen or hydroxy;

$R^4$ is hydroxy or amino;

$R^5$ is amino or methylamino;

$R^7$ is hydroxy or methyl;

$R^8$ is hydrogen, hydroxymethyl, or carbamoyloxymethyl; and the dotted line represents the presence of absence of a double bond and a pharmaceutically acceptable salt thereof.

2. A compound claim in claim 1, wherein R is 2-azetidinyl.

3. A compound claimed in claim 1, wherein R is 3-azetidinyl.

4. A compound claimed in claim 1, wherein R is 2-pyrrolidinyl.

5. A compound claimed in claim 1, wherein R is 3-pyrrolidinyl.

6. A compound claimed in claim 1, wherein R is 3-piperidinyl.

7. A compound claimed in claim 1, wherein R is 2-piperazinyl.

8. A compound claimed in claim 1, wherein $R^8$ is hydrogen or hydroxymethyl.

9. A compound claimed in claim 1, wherein $R^1$ is aminomethyl or hydroxymethyl and $R^8$ is hydrogen or hydroxymethyl.

10. A compound claimed in claim 1, wherein $R^1$ is aminomethyl or hydroxymethyl and $R^8$ is hydroxymethyl.

11. A compound claimed in claim 1, wherein $R^1$ is aminomethyl, $R^2$ is hydroxy, $R^5$ is amino, $R^6$ is hydrogen, $R^7$ is hydroxy, and $R^8$ is hydroxymethyl.

12. A compound claimed in claim 1, namely 1-N-[α-hydroxy-α-(azetidin-2-yl)acetyl]tobramycin.

13. A compound claimed in claim 1, namely 1-N-[α-hydroxy-α-(azetidin-3-yl)acetyl]tobramycin.

14. A compound claimed in claim 1, namely 1-N-[α-hydroxy-α-(pyrrolidin-2-yl)acetyl]tobramycin.

15. A compound claimed in claim 1, namely 1-N-[α-hydroxy-α-(pyrrolidin-3-yl)acetyl]tobramycin.

16. A compound claimed in claim 1, namely 1-N-[α-hydroxy-α-(piperidin-3-yl)acetyl]tobramycin.

17. A compound claimed in claim 1, namely 1-N-[α-hydroxy-α-(piperazin-2-yl)acetyl]tobramycin.

18. A composition comprising an effective amount of a compound claimed in any of above claims 1 to 17 and pharmaceutically acceptable carriers.

19. A method for treating bacterial infectious diseases of humans or other species of animals which comprises administering to a host suffering from such bacterial infectious disease a bactericidally effective amount of a compound claimed in any of above claims 1 to 17.

* * * * *